United States Patent
Ryu et al.

(10) Patent No.: US 10,488,333 B2
(45) Date of Patent: Nov. 26, 2019

(54) OPTICAL SENSOR, MANUFACTURING METHOD THEREOF, AND FLUID ANALYSIS METHOD USING THE SAME

(71) Applicant: KOREA INSTITUTE OF SCIENCE AND TECHNOLOGY, Seoul (KR)

(72) Inventors: Yong-Sang Ryu, Seoul (KR); Chulki Kim, Seoul (KR); Young Min Jhon, Seoul (KR); Sin-Doo Lee, Seoul (KR); Eui-Sang Yu, Seoul (KR); Jae Hun Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 15/935,055

(22) Filed: Mar. 26, 2018

(65) Prior Publication Data
US 2019/0025204 A1  Jan. 24, 2019

(30) Foreign Application Priority Data

Jul. 24, 2017 (KR) .................. 10-2017-0093618
Oct. 12, 2017 (KR) .................. 10-2017-0132694

(51) Int. Cl.
*G01N 21/41* (2006.01)
*H01J 37/305* (2006.01)
(Continued)

(52) U.S. Cl.
CPC ......... *G01N 21/4133* (2013.01); *G01N 21/27* (2013.01); *G01N 21/554* (2013.01);
(Continued)

(58) Field of Classification Search
CPC .. G01N 21/27; G01N 21/4133; G01N 21/554; H01J 2237/3174; H01J 37/3056; H01L 31/09
(Continued)

(56) References Cited

U.S. PATENT DOCUMENTS 8,154,722 B2   4/2012 Yamada et al.
2007/0210349 A1*  9/2007 Lu .......................... B82Y 5/00
                                                                257/252
(Continued)

FOREIGN PATENT DOCUMENTS

JP      2007263955 A   10/2007
JP       201555482 A    3/2015
(Continued)

OTHER PUBLICATIONS

Jiancai Xue et al., "Scalable, full-colour and controllable chromotropic plasmonic printing," Nature Communications, Nov. 16, 2015, pp. 1-9, vol. 6, Article 8906, Macmillan Publishers Limited.
(Continued)

*Primary Examiner* — Tri T Ton
(74) *Attorney, Agent, or Firm* — Cantor Colburn LLP

(57) ABSTRACT

A method for manufacturing an optical sensor includes forming a reflective metal layer on a substrate, forming an insulator layer on the reflective metal layer, inducing self-assembly of a metal nanostructure layer on the insulator layer, and selectively etching the insulator layer through a reactive ion etching process to form a plurality of pillars and a plurality of spaces defined by the plurality of pillars. The method for manufacturing a plasmonic optical sensor according to this embodiment facilitates the formation of nanostructures difficult to pattern and form on the large scale at a low cost, and provides a plasmonic optical sensor with repeatability.

8 Claims, 13 Drawing Sheets

(51) Int. Cl.
*G01N 21/552* (2014.01)
*G01N 21/27* (2006.01)
*H01L 31/09* (2006.01)

(52) U.S. Cl.
CPC .......... *H01J 37/3056* (2013.01); *H01L 31/09* (2013.01); *H01J 2237/3174* (2013.01)

(58) Field of Classification Search
USPC .................................................. 356/128–137
See application file for complete search history.

(56) References Cited

U.S. PATENT DOCUMENTS

| | | | |
|---|---|---|---|
| 2008/0129980 A1* | 6/2008 | Dhawan | G01C 3/00 356/12 |
| 2015/0070693 A1 | 3/2015 | Sugimoto et al. | |
| 2017/0018685 A1* | 1/2017 | Cho | H01L 33/007 |

FOREIGN PATENT DOCUMENTS

| | | |
|---|---|---|
| KR | 1020100002960 A | 1/2010 |
| KR | 101205392 B1 | 11/2012 |
| KR | 1020160038207 A | 4/2016 |
| KR | 1020160038209 A | 4/2016 |
| KR | 101621437 B1 | 5/2016 |
| KR | 1020160107914 A | 9/2016 |
| KR | 1020160125806 A | 11/2016 |
| KR | 1020170012868 A | 2/2017 |
| KR | 1020170053189 A | 5/2017 |

OTHER PUBLICATIONS

Young-Jae Oh et al., "Glass Nanopillar Arrays with Nanogap-Rich Silver Nanoislands for Highly Intense Surface Enhanced Raman Scattering," Advanced Materials, 2012, pp. 2234-2237, vol. 24.

Yuqi Zhang et al., "Photonic sensing of organic solvents through geometric study of dynamic reflection spectrum," Nature Communications, Jun. 17, 2015, pp. 1-7, vol. 6, Article 7510, Macmillan Publishers Limited.

Zhengqi Liu et al., "Automatically Acquired Broadband Plasmonic-Metamaterial Black Absorber during the Metallic Film-Formation," ACS Applied Materials & Interfaces, Feb. 13, 2015, pp. 4962-4968, vol. 7, No. 8.

* cited by examiner

Color shift in the visible light range

OPTICAL SENSOR, MANUFACTURING METHOD THEREOF, AND FLUID ANALYSIS METHOD USING THE SAME

DESCRIPTION OF GOVERNMENT-SPONSORED RESEARCH AND DEVELOPMENT

This research is done in support of Nano Material technology development program (Development of DNA based all-optical control device, Project series number: 2016938420) of Ministry of Science and ICT under the supervision of Industry-academic cooperation foundation, Yonsei university.

CROSS-REFERENCE TO RELATED APPLICATION

This application claims priority to Korean Patent Application No. 10-2017-0093618, filed on Jul. 24, 2017 and No. 10-2017-0132694, filed on Oct. 12, 2017 and all the benefits accruing therefrom under 35 U.S.C. § 119, the contents of which in its entirety are herein incorporated by reference.

BACKGROUND

1. Field

The present disclosure relates to an optical sensor, a manufacturing method thereof and a fluid analysis method using the same, and more particularly, to a nanostructure-based color changing optical sensor, a manufacturing method thereof and a fluid analysis method using the same.

2. Description of the Related Art

The field of nanoplasmonics using resonance phenomena brought about by particles incident through metal surfaces has applications in selective light absorption and high sensitivity sensor chip development as well as in various fields, and is extending its aspects. Surface plasmon resonance (SPR) sensor contains a surface plasmon layer, or a metal thin film, which is placed on the flat surface of a glass prism, and a target sample is placed below. When a polarized optical signal is reflected on the surface of the metal thin film through the prism, surface plasmon resonance phenomena occur, an optical signal incident at a specific angle loses its energy and travels along the interface of the metal thin film and the target sample, and a surface plasmon resonance angle may be obtained by measuring the intensity of the reflected optical signal energy.

Generally, in the case of an optical sensor using plasmonics, nanostructures are made and a target material is brought into contact with the structures, and the optical sensor has been used as a sensor exploiting a red shift of peak wavelength or deep wavelength of the corresponding incident light and reflected light. However, its target wavelength range is limited to infrared wavelength, mid-infrared wavelength range, or Terahertz range.

To identify colors in the visible light range, a wavelength shift of 100 nm or more is essential, and to this end, nanostructure configuration and other methods have been proposed. That is, development of sensors in the visible light range succeeded by implementing light of the full color range using photonic crystal structures or based on plasmonic phenomena, but primarily using an interference phenomenon of incident light and reflected light and constructive interference (CI) and destructive interference (DI), however expensive nano patterning technique required limits the widespread use and commercialization of technology.

SUMMARY

The present disclosure is designed to solve the above-mentioned problem, and therefore the present disclosure provides an optical sensor using nanostructures that can be fabricated without a complex and costly process, a manufacturing method thereof, and a fluid analysis method using the same.

A method for manufacturing an optical sensor according to an embodiment of the present disclosure includes forming a reflective metal layer on a substrate, forming an insulator layer on the reflective metal layer, inducing self-assembly of a metal nanostructure layer on the insulator layer, and selectively etching the insulator layer to form a plurality of pillars and a plurality of spaces defined by the plurality of pillars.

In an embodiment, the plurality of pillars may include a hydrophobic material.

In an embodiment, the hydrophobic material may be amorphous fluoropolymer, and a refractive index of the plurality of pillars and a refractive index of the plurality of spaces may be different.

In an embodiment, the reflective metal layer may be a gold thin film layer, and a metal applied to the self-assembly of the metal nanostructure layer may be gold.

In an embodiment, the forming of the reflective metal layer and the inducing of the self-assembly of the metal nanostructure layer may be performed through a thermal evaporation process, and a thermal evaporation rate of the reflective metal layer may be faster than a thermal evaporation rate of the nanostructure layer.

In an embodiment, the thermal evaporation rate in inducing the self-assembly of the metal nanostructure layer may be 0.3 Å/s.

An optical sensor according to an embodiment of the present disclosure includes a substrate, a reflective metal layer disposed on the substrate, an insulator layer disposed on the reflective metal layer and a metal nanostructure layer disposed on the insulator layer, wherein the metal nanostructure layer is a nanoisland network structure in which a plurality of nanoislands is connected, and the insulator layer includes a plurality of pillars and a plurality of spaces defined by the plurality of pillars, and the plurality of spaces is filled with a first fluid having a refractive index that is different from a refractive index of the plurality of pillars.

In an embodiment, the plurality of pillars may include a hydrophobic material.

In an embodiment, the hydrophobic material may be amorphous fluoropolymer.

In an embodiment, the reflective metal layer may be a gold thin film layer, and a metal applied to self-assembly of the metal nanostructure layer may be gold.

In an embodiment, when a second fluid to be analyzed is introduced, the first fluid in the plurality of spaces may be replaced with the second fluid.

In an embodiment, when the plurality of spaces is filled with the second fluid, effective dielectric constant and refractive index values of the insulator layer change, and resonance wavelength in a reflection spectrum and a thickness value of the insulator layer where light permeates and bounces off may be adjusted.

In an embodiment, the resonance wavelength shift of the reflection spectrum may be made in visible light range.

A fluid analysis method using an optical sensor including a substrate, a reflective metal layer disposed on the substrate, an insulator layer disposed on the reflective metal layer and a metal nanostructure layer disposed on the insulator layer, wherein the metal nanostructure layer is a nanoisland network structure in which a plurality of nanoislands is connected, the insulator layer includes a plurality of pillars and a plurality of spaces defined by the plurality of pillars, and the plurality of spaces are filled with a fluid having a refractive index that is different from a refractive index of the plurality of pillars, includes preparing the optical sensor, introducing a sample into the plurality of spaces to replace the fluid, and analyzing a refractive index of the sample by identifying color displayed on the optical sensor.

In an embodiment, the fluid analysis method using an optical sensor may further include defining the sample based on the refractive index of the sample.

In an embodiment, the analyzing of the refractive index of the sample may further include determining if the sample is toxic by identifying color that a toxic material displays in the optical sensor.

The optical sensor according to an embodiment of the present disclosure can be manufactured without a complex and costly process because metal nanostructures are fabricated on a hydrophobic dielectric layer using self-assembly phenomenon technique.

Additionally, because a device can be implemented on the large scale by a simple process, it is possible to make a label-free color-based optical sensor with visibility in high yield at a low cost.

BRIEF DESCRIPTION OF THE DRAWINGS

The above and other features and aspects of the present invention will become more apparent by describing in detail example embodiments thereof with reference to the attached drawings in which.

DETAILED DESCRIPTION

Figure 1:
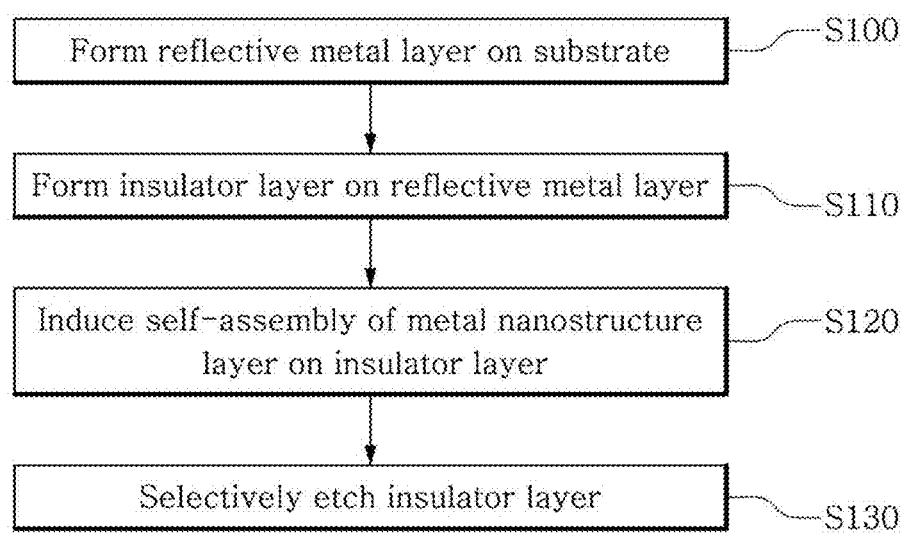
FIG. 1 is a flowchart of a method for manufacturing an optical sensor according to an embodiment of the present disclosure.

The present disclosure is described in detail as below with reference to the accompanying drawings in which particular embodiments for carrying out the present disclosure are shown for illustration. These embodiments are described in sufficient detail to enable those skilled in the art to practice the present disclosure. Various embodiments of the present disclosure are different from each other, but they do not need to be exclusive. For example, a particular shape, structure and characteristic described herein, in connection with one embodiment, may be implemented in other embodiments without departing from the spirit and scope of the present disclosure. Further, modification may be made to the position or arrangement of respective elements in each disclosed embodiment without departing from the spirit and scope of the present disclosure. Therefore, the following detailed description is not made in a restrictive sense, and the scope of the present disclosure is only defined by the appended claims, if appropriately described, along with the full scope of equivalents to which the claims are entitled. In the drawings, similar reference numerals denote same or similar functions throughout many aspects.

The terms as used herein are general terms selected as those being now used as widely as possible in consideration of functions, but they may vary depending on the intention of those skilled in the art or the convention or the emergence of new technology. Additionally, in certain cases, there may be terms arbitrarily selected by the applicant, and in this case, the meaning will be described in the corresponding description part of the specification. Accordingly, the terms as used herein should be interpreted based on the substantial meaning of the terms and the content throughout the specification, rather than simply the name of the terms.

Figure 2:
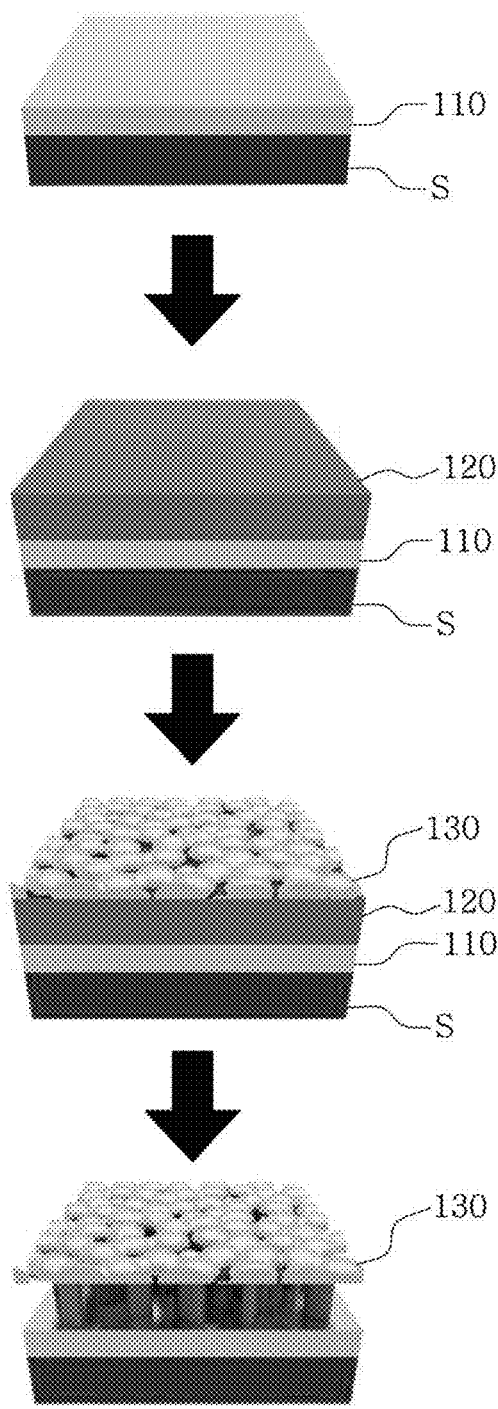
FIG. 2 is a schematic diagram of the method for manufacturing an optical sensor.
Figure 3:
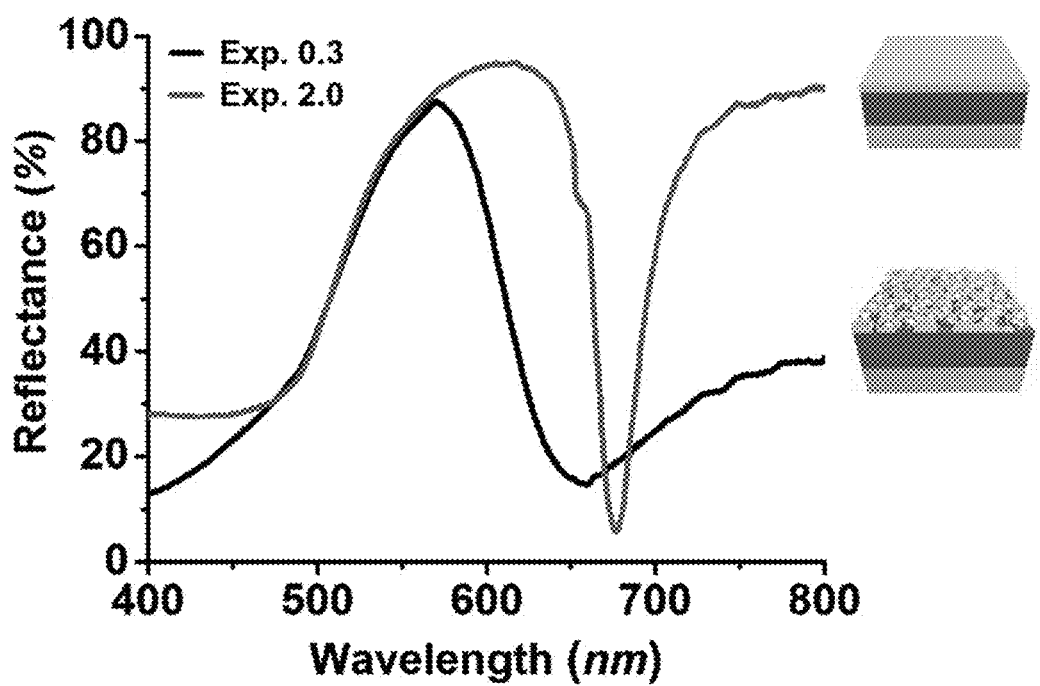
FIG. 3 is a graph showing the comparison of structures and changes in optical properties as a function of a formation rate of a metal nanostructure layer.
Figure 4:
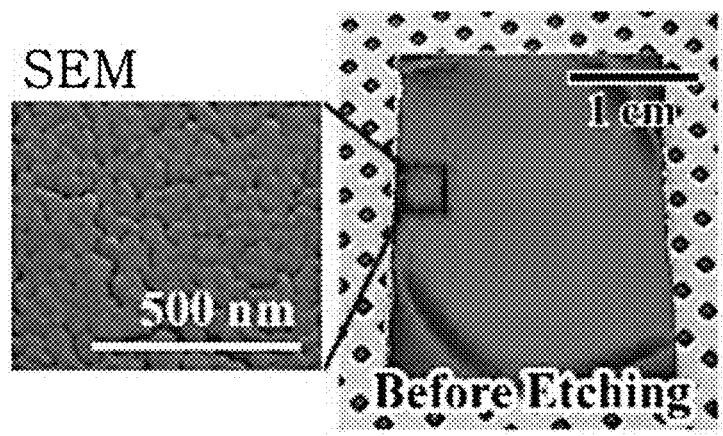
FIG. 4 is a plane scanning electron microscopy (SEM) photographic image of a metal nanostructure layer.
Figure 5:
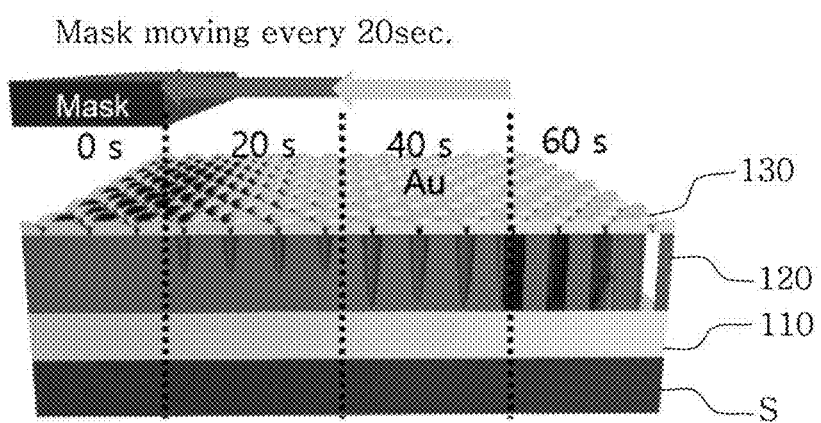
FIG. 5 is a diagram showing changes in structure of an insulator layer as an ionic etching process proceeds.
Figure 6:
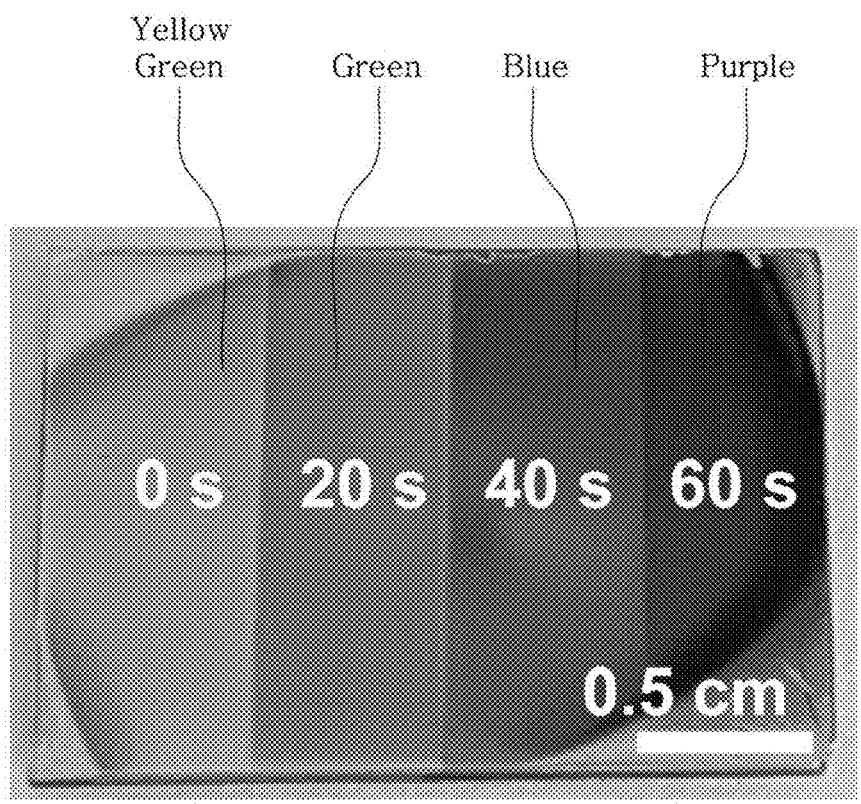
FIG. 6 is a diagram showing changes in surface color of an insulator layer as an ionic etching process proceeds.
Figure 7:
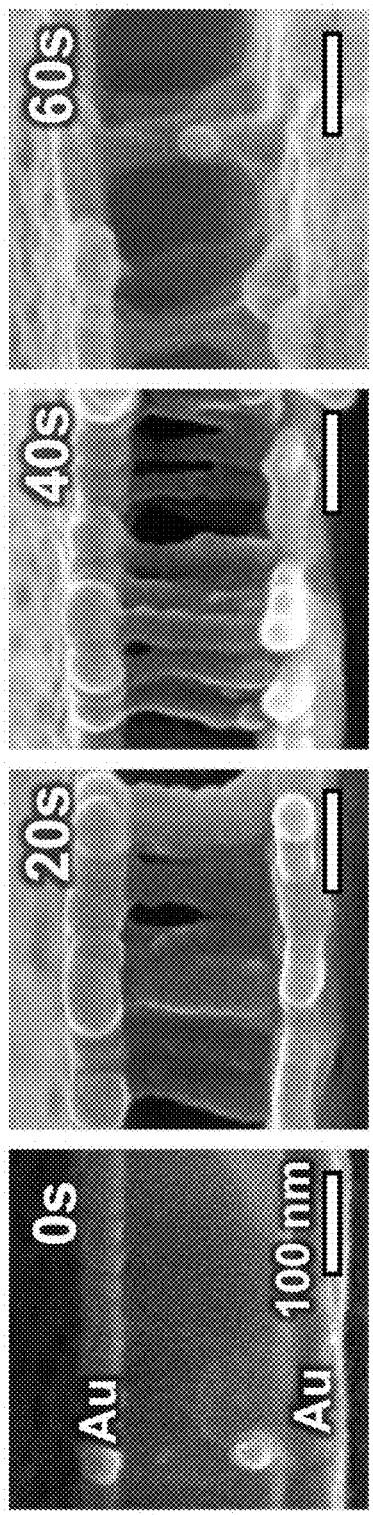
FIG. 7 is a side SEM photographic image showing changes in structure of an insulator layer as an ionic etching process proceeds.

FIG. 1 is a flowchart of a method for manufacturing an optical sensor according to an embodiment of the present disclosure, FIG. 2 is a schematic diagram of the method for manufacturing an optical sensor, FIG. 3 is a graph showing the comparison of structures and changes in optical properties as a function of a formation rate of a metal nanostructure layer, FIG. 4 is a plane scanning electron microscopy (SEM) photographic image of a metal nanostructure layer, FIG. 5 is a diagram showing changes in structure of an insulator layer as an ionic etching process proceeds, FIG. 6 is a diagram showing changes in surface color of an insulator layer as an ionic etching process proceeds, and FIG. 7 is a side SEM photographic image showing changes in structure of an insulator layer as an ionic etching process proceeds.

Referring to FIGS. 1 to 7, the method for manufacturing an optical sensor according to an embodiment of the present disclosure includes forming a reflective metal layer on a substrate (S100), forming an insulator layer on the reflective metal layer (S110), inducing the self-assembly of a metal nanostructure layer on the insulator layer (S120), and selectively etching the insulator layer through a reactive ion etching process (S130).

First, a reflective metal layer is formed on a substrate (S100).

The substrate may be a flat rigid substrate. The substrate may be a glass substrate, but is not limited thereto, and may include all types of base substrates made of plastics, silicon or other polymers, on which metal deposition may be performed.

The reflective metal layer 110 may be formed on the substrate. The reflective metal layer 110 may be formed via a thermal evaporation process, but is not limited thereto, and may be also formed by a process such as plating and sputtering. The reflective metal layer 110 may include a material such as Ag, Ni, Al, Rh, Pd, Ir, Ru, Mg, Zn, Pt and Au, alone or alloys. Preferably, the reflective metal layer 110 may be a single thin film layer made of gold (Au). The reflective metal layer 110 may be formed with the thickness of 100 nm. The reflective metal layer 110 may reflect light entering from the top, and concentrate light on the insulator layer 120 and the metal nanostructure layer 130, and accordingly may improve the nanoplasmonic effects.

Subsequently, an insulator layer is formed the reflective metal layer (S110). The insulator layer 120 may be formed on the reflective metal layer 110. The insulator layer 120 may be formed through a spin coating process, but is not limited thereto, and may be formed by other processes such as spray coating and liquid deposition. In some embodiments, a planarization process for planarizing the reflective metal layer 110 may be performed before forming the insulator layer 120.

The insulator layer 120 may include a hydrophobic material. At least the surface area of the insulator layer 120 may be hydrophobic. The hydrophobic material may be amorphous fluoropolymer and the insulator layer 120 may be transparent over the whole. The refractive index n of the insulator layer 120 may be 1.34. Preferably, the insulator layer 120 may be formed with a thickness of 140 nm to 180 nm by applying amorphous fluoropolymer.

Subsequently, self-assembly of a metal nanostructure layer is induced (S120).

The metal nanostructure layer 130 may be formed on the insulator layer 120. The metal nanostructure layer 130 may be a nanoisland network structure in which a plurality of metal nanoislands is connected. Each metal nanoisland may be a cluster of a predetermined size or more. The metal applied to the metal nanostructure layer 130 may be any one selected from the group consisting of platinum, gold, silver, aluminum, and their combination. The metal nanostructure layer 130 may be preferably gold (Au), and may be made of the same metal as the metal used for the reflective metal layer 110.

The metal nanostructure layer 130 may be produced through a thermal evaporation process. The thermal evaporation process for forming the metal nanostructure layer 130 may be performed at a lower rate than the thermal evaporation process for forming the reflective metal layer 110. Because the surface of the insulator layer 120 is hydrophobic, nanoisland structures of a predetermined size may be formed in a distributed manner over the insulator layer 120 at the early stage of deposition. The step of forming the metal nanostructure layer (S120) may perform deposition on the initially formed nanoisland structures, rather than coating over the entire surface of the insulator layer 120. The step of forming the metal nanostructure layer (S120) may be performed at the metal deposition rate of 0.3 Å/s that is noticeably reduced in comparison with the metal deposition rate of 1-2 Å/s according to the conventional deposition method. The metal deposition rate of 0.3 Å/s may induce the self-assembly of the metal nanoislands. The nanoislands whose diameter increases as the thermal evaporation process proceeds may be connected to adjacent nanoislands to form a nanoisland network. The preferred thickness of the metal nanostructure layer 130 may be 27 nm to 33 nm. More preferred thickness of the metal nanostructure layer 130 may be 30 nm.

As shown in FIG. 4, the nanoisland network is an array of nanoislands that are grown and connected with each other, and the metal nanostructure layer 130 may include a plurality of nano-apertures through which the surface of the insulator layer 120 is exposed to the outside. The corresponding nano-aperture may be an area in which the metal is not deposited and a connection between the nanoislands is not established.

FIG. 3 shows the comparison of resultant structures and optical properties as a function of the deposition rate of the metal nanostructure layer 130 between i) the metal nanostructure layer 130 formed at the rate of 0.3 Å/s and ii) the metal nanostructure layer 130 formed at the rate of 2.0 Å/s. It can be seen that i) when the metal nanostructure layer 130 is formed at the rate of 0.3 Å/s, the metal nanostructure layer 130 forms a nanoisland network as described above, and includes nano-apertures. In contrast, it can be seen that ii) when the metal nanostructure layer 130 is formed at the rate of 2.0 Å/s, the metal nanostructure layer 130 is formed as a thin film layer on the insulator layer 120, and does not have nano-apertures. It can be seen that i) the metal nanostructure layer 130 of a nanoisland network and ii) the metal nanostructure layer 130 of a thin film layer exhibit different optical properties (reflectance) based on whether there are nano-apertures or not. Additionally, only the metal nanostructure layer 130 of a nanoisland network may go through a selective reactive ion etching process as described below via the nano-apertures.

The insulator layer is selectively etched through a reactive ion etching process (S130).

The metal nanostructure layer 130 may act as an etching mask. In the reactive ion etching process, it is required that reaction with the metal nanostructure layer 130 does not occur, and the metal nanostructure layer 130 is not removed. Accordingly, selective etching may be performed on the insulator layer 120 having no metal nanoisland on top to form the nanostructures according to the present disclosure.

The insulator layer 120 may be etched, corresponding to the nano-apertures of the metal nanostructure layer 130. That is, the insulator layer 120 having the metal nanoislands formed on top may remain as pillars of a predetermined width, and the insulator layer corresponding to the nano-apertures may form a space into which a fluid is introduced. As shown in FIGS. 5 and 7, as the etching process (S130) proceeds, the insulator layer 120 forms an etched space, and the size of the etched space will be larger. Additionally, when the etched space of the insulator layer 120 with the refractive index (n=1.34) having a predetermined size is replaced with air, the optical properties of the insulator layer 120 may change. Here, the refractive index (n=1.00) of air may be lower than the refractive index of the insulator layer 120, and a refractive index distribution inside the insulator layer 120 may change. As shown in FIG. 6, it can be seen that the color changes from yellow green to purple as the reactive ion etching process proceeds.

The nanostructures formed in the insulator layer 120 may further improve the sensitivity of the plasmonic sensor to surrounding refractive index in the absorption wavelength range, maximize the wavelength shift in the visible light range based on plasmonic phenomena, and induce the visible color change.

Additionally, a serial nano process, such as electron beam lithography and focused ion beam, which has been used to fabricate metal nanostructures, is difficult to be used in large scale applications, and requires high costs.

As opposed to this, the method for manufacturing a plasmonic optical sensor according to this embodiment fabricates the metal nanostructures on the hydrophobic dielectric layer using self-assembly phenomenon technique, so there is no need for a complex and costly process, the nanostructures may be implemented on the large scale by a simple process, and structure that maximizes plasmonic phenomena in the insulator layer using the metal nanostructures as a mask may be formed.

That is, the method for manufacturing a plasmonic optical sensor according to this embodiment may facilitate the formation of nanostructures difficult to pattern and form on the large scale at a low cost, and provide a plasmonic optical sensor with repeatability.

Hereinafter, an optical sensor according to an embodiment of the present disclosure will be described.

The optical sensor 10 according to an embodiment of the present disclosure may be produced by the above described manufacturing method of FIGS. 1 to 7, and for easy description, a reference may be made to FIGS. 1 to 7.

Figure 8:
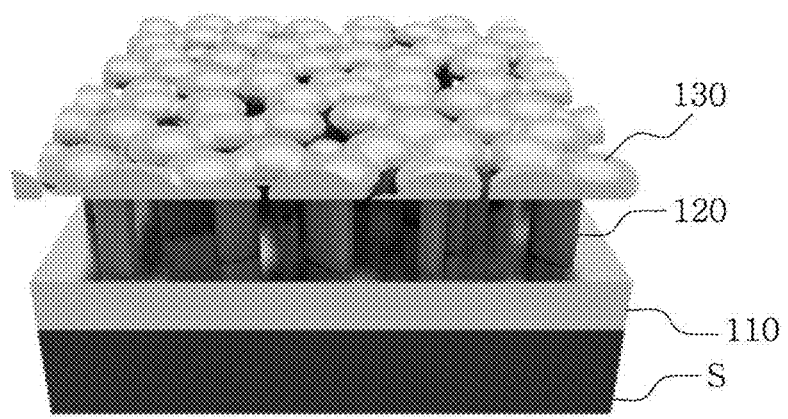
FIG. 8 is a schematic diagram showing the optical sensor according to an embodiment of the present disclosure.
Figure 9A:
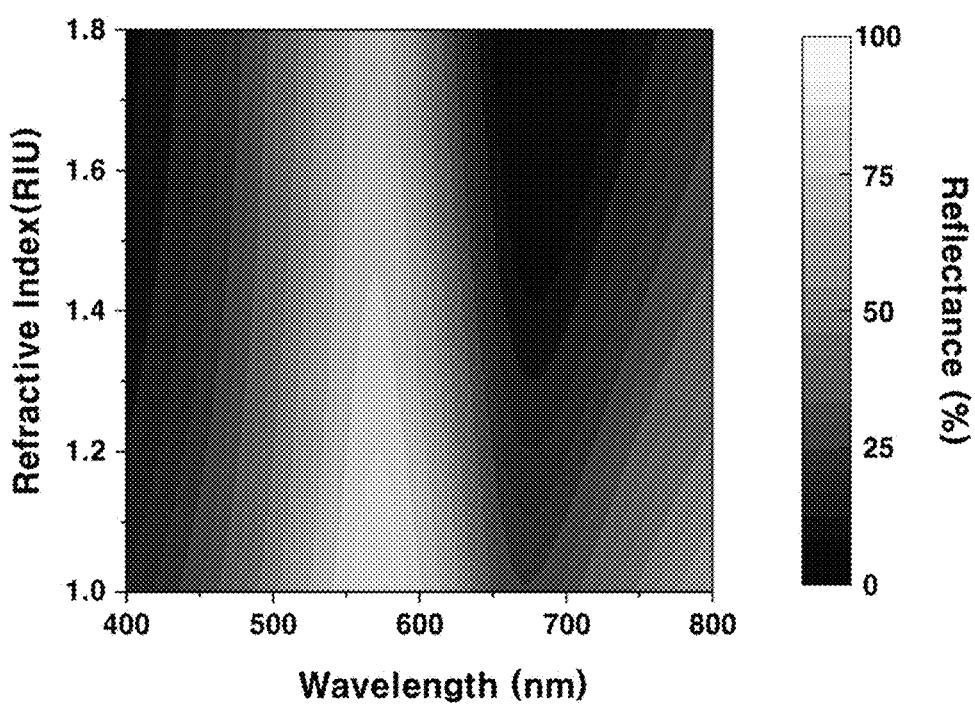
FIGS. 9A and 9B are a graph showing the optical properties of the optical sensor according to an embodiment of the present disclosure.
Figure 9B:
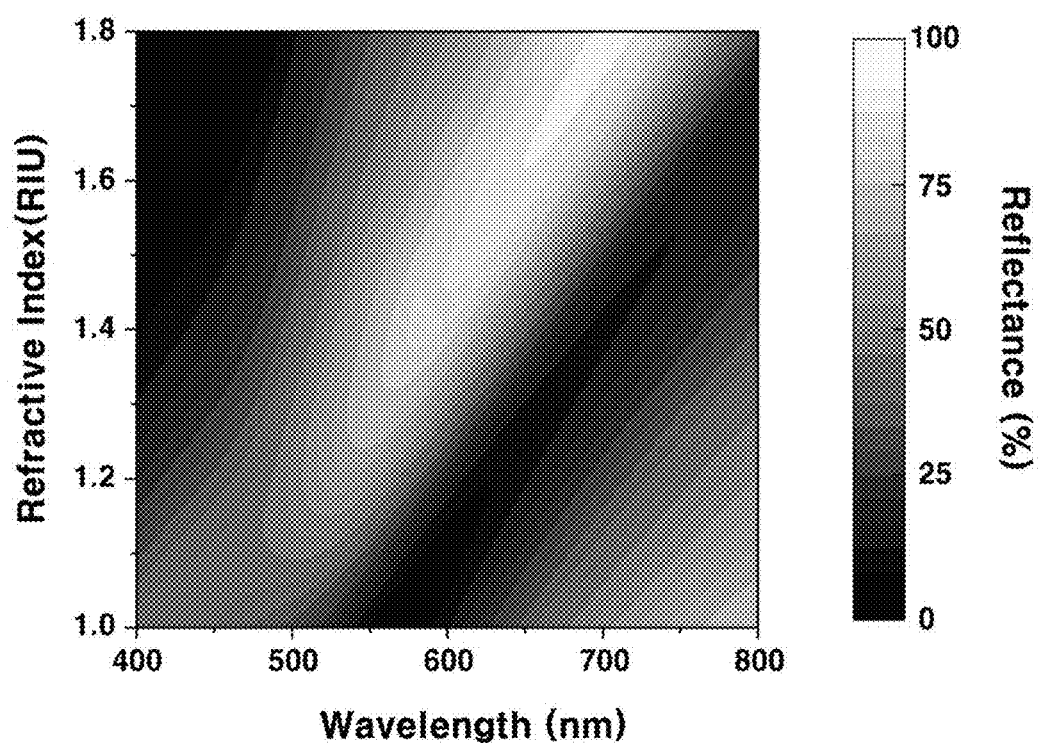
Figure 10A:
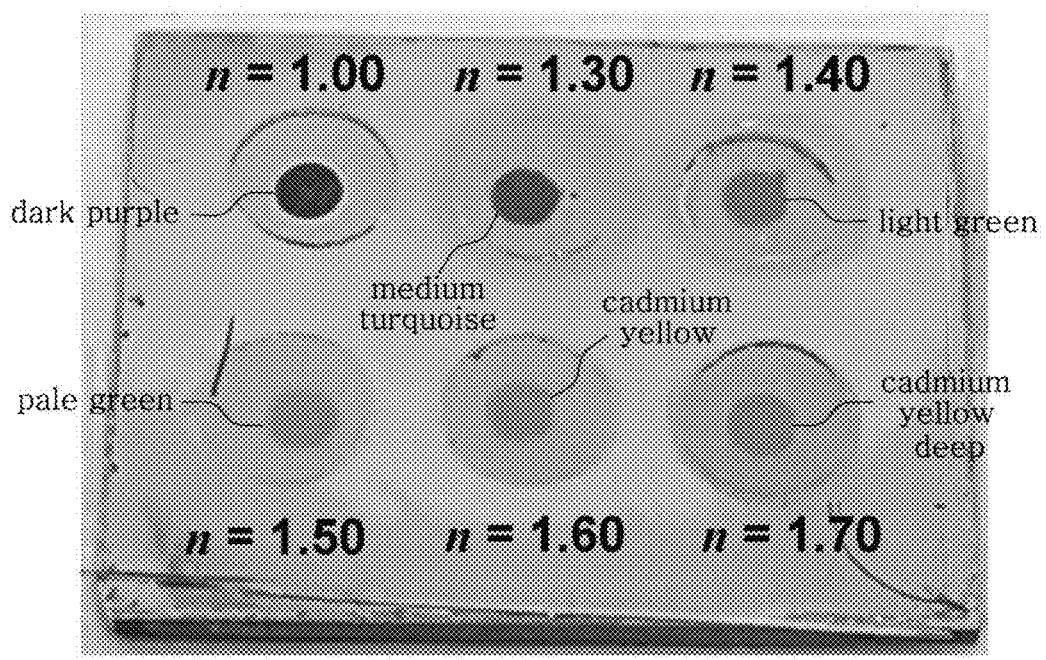
FIGS. 10A and 10B are a diagram showing the comparison of color changes in the optical sensor according to an embodiment of the present disclosure.
Figure 10B:
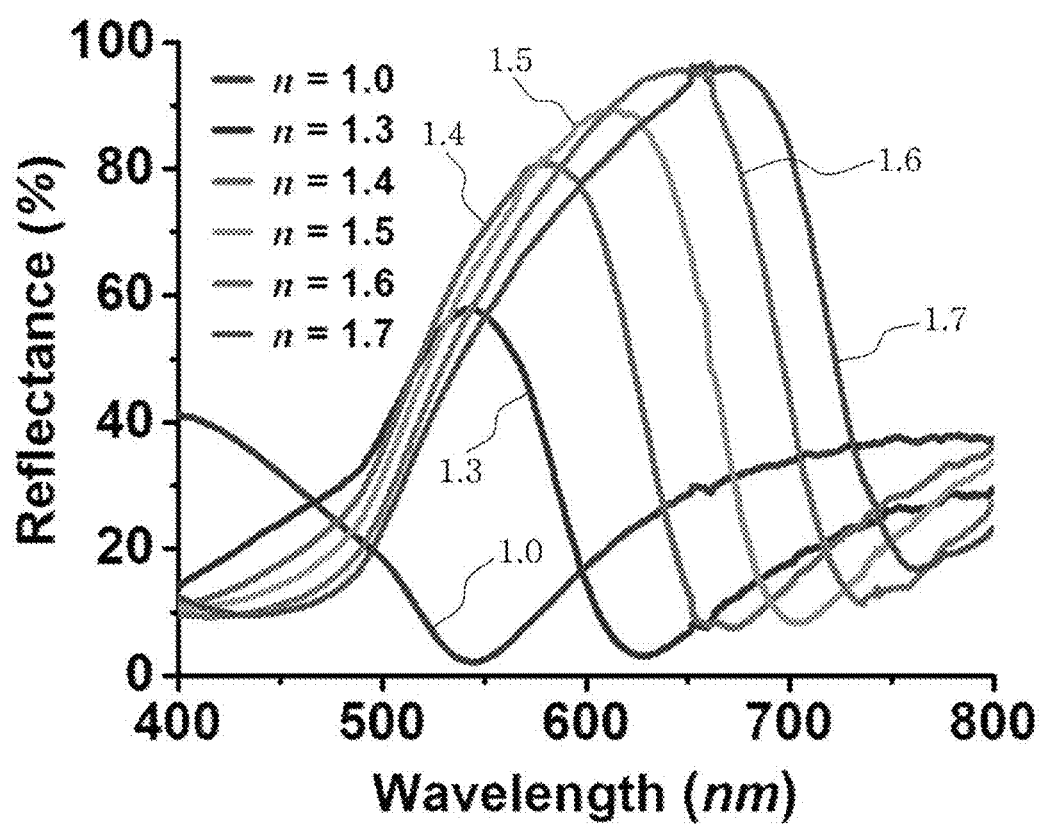

FIG. 8 is a schematic diagram showing the optical sensor according to an embodiment of the present disclosure, FIGS. 9A and 9B are a graph showing the optical properties of the optical sensor according to an embodiment of the present disclosure, and FIGS. 10A and 10B are a diagram showing the comparison of color changes in the optical sensor according to an embodiment of the present disclosure.

Referring to FIGS. 8 to 10B, the optical sensor 10 according to an embodiment of the present disclosure includes a substrate, a reflective metal layer 110, an insulator layer 120 and a metal nanostructure layer 130, and the insulator layer may include a partially etched space.

The substrate may be a flat rigid substrate. The substrate may be a glass substrate, but is not limited thereto, and may be a base substrate made of plastics, silicon or other polymers.

The reflective metal layer 110 may be disposed on the substrate. The reflective metal layer 110 may be formed through a thermal evaporation process, but is not limited thereto, and may be also formed by a process such as plating and sputtering. The reflective metal layer 110 may include a material such as Ag, Ni, Al, Rh, Pd, Ir, Ru, Mg, Zn, Pt and Au, alone or alloys. Preferably, the reflective metal layer 110 may be a single thin film layer made of gold (Au), and its thickness may be 100 nm. The reflective metal layer 110 may reflect light entering from the top, and concentrate light on the insulator layer 120 and the metal nanostructure layer 130, and accordingly may improve the nanoplasmonic effects.

The insulator layer 120 may be disposed on the reflective metal layer 110. The insulator layer 120 may have a partially etched shape. The insulator layer 120 is formed as a thin film through a spin coating process, and is partially etched through a reactive ion etching process using the metal nanostructure layer 130 as a mask.

The insulator layer 120 may include a plurality of pillars p made of a hydrophobic material and a plurality of spaces v defined by the plurality of pillars. Here, the plurality of spaces v may be filled with a predetermined fluid, and the refractive index of the pillars p may be different from the refractive index of the fluid filled in the plurality of spaces v. For example, the pillars p may be made of amorphous fluoropolymer and have the refractive index of 1.34, and the spaces v may be filled with air and have the refractive index of 1.00.

The insulator layer 120 may be transparent over the whole, and the overall thickness may be 140 nm to 180 nm.

The metal nanostructure layer 130 may be disposed on the insulator layer 120. The metal nanostructure layer 130 may be a nanoisland network structure in which a plurality of metal nanoislands is connected. Each metal nanoisland may be a cluster of a predetermined size or more. The nanoisland network is an array of nanoislands that are grown and connected with each other, and the metal nanostructure layer 130 may include a plurality of nano-apertures through which the surface of the insulator layer 120 is exposed to the outside. The corresponding nano-aperture may be an area in which the metal is not deposited and a connection between the nanoislands is not established.

The metal nanostructure layer 130 is formed by performing a thermal evaporation process at a low rate enough to induce the self-assembly of the metal nanoislands, and the preferred thickness of the metal nanostructure layer 130 may be 27 nm to 33 nm. More preferred thickness of the metal nanostructure layer 130 may be 30 nm.

The metal applied to the metal nanostructure layer 130 may be any one selected from the group consisting of platinum, gold, silver, aluminum and their combination. The metal applied to the metal nanostructure layer 130 may be preferably gold (Au), and may be the same as the metal used for the reflective metal layer 110. As described above, the metal nanostructure layer 130 may act as a mask of the reactive ion etching process. Additionally, the metal nanostructure layer 130 may allow nanogap plasmonic phenomena to occur between the nanostructures formed through self-assembly.

The optical sensor 10 according to an embodiment of the present disclosure is an improvement of the conventional metal-dielectric-metal (MDM) sandwich structure. That is, the optical sensor 10 according to an embodiment of the present disclosure evolves from nanoplasmonic phenomena used to improve the absorption rate, and may maximize visible light wavelength range shift phenomena based on plasmonic phenomena through selective etching of the insulator layer that has been known as playing an important role in giving rise to plasmonic phenomena, thereby inducing a color change in the visible light range.

The insulator layer 120 according to this embodiment has empty spaces (v) formed by etching a hydrophobic material (n: 1.34), and a value of effective refractive index of the insulator layer that is an important factor in causing plasmonic phenomena may change depending on the extent to which the spaces v of the insulator layer 120 are replaced with air (n: 1.00), directly affecting the path along which light permeates and passes through, thereby selectively absorbing light of a specific range of wavelengths and emitting light of the other wavelengths. Additionally, when the spaces v of the insulator layer 120 are replaced with a fluid having a different refractive index value, the effective refractive index value of the insulator layer 120 may change in response to the intrinsic refractive index of each fluid, and accordingly, the wavelength of visible light absorbed may vary.

FIG. 9A is a graph showing the optical properties of the optical sensor in which a reactive ion etching process is not performed on the insulator layer, and FIG. 9B is a graph showing the optical properties of the optical sensor having nano spaces formed by performing a reactive ion etching process on the insulator layer.

The optical sensor of FIG. 9A has maximum absorption at the wavelength of 675 nm irrespective of the refractive index of an introduced fluid and its optical properties are less sensitive to an fluid introduced from the outside, while the optical sensor of FIG. 9B exhibits changes in the maximum absorption in the wavelength range between 500 nm and 800 nm in response to the refractive index of an introduced fluid. It can be seen that such optical properties are proportional to the refractive index of an introduced fluid.

FIG. 10A is a diagram showing a color change of the optical sensor with different refractive indices n of fluids, and FIG. 10B is a graph showing the optical properties of the fluids having different refractive indices n.

The optical sensors 10 are exposed to air (n=1.00) and liquids having five refractive indices (n=1.30, 1.40, 1.50, 1.60, 1.70), and then color changes are identified and the optical properties of each optical sensor 10 are identified. As shown in FIG. 10A, the optical sensor 10 according to this embodiment may display different colors depending on the refractive index of the introduced fluid. In the optical sensor 10, the resonance wavelength may be shifted in the reflection spectrum by a predetermined interval in response to the refractive index of each fluid as shown in FIG. 10B, and color displayed by the optical sensor 10 may change, which corresponds to a shift in the visible light range.

The optical sensor according to this embodiment causes a wavelength shift of 200 nm or more in the visible light range, and may identify various liquids by colors in the visible light range. Additionally, when exposed to an environment, the optical properties change quickly, and when out of the corresponding environment, the optical sensor restores to original condition, ensuring high recyclability, and can be used on site without any additional element, thereby providing high on-site.

Hereinafter, a fluid analysis method using an optical sensor according to an embodiment of the present disclosure will be described.

Figure 11:
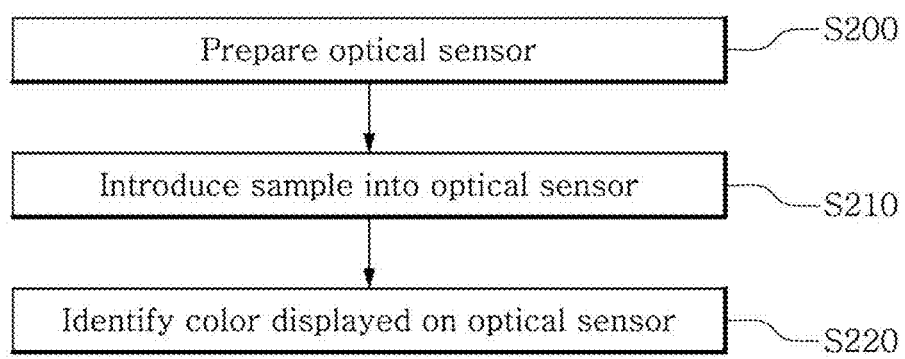
FIG. 11 is a flowchart of the fluid analysis method using an optical sensor according to an embodiment of the present disclosure.

FIG. 11 is a flowchart of the fluid analysis method using an optical sensor according to an embodiment of the present disclosure. The fluid analysis method using an optical sensor according to an embodiment of the present disclosure includes preparing an optical sensor (S200), introducing a sample into the optical sensor (S210), and identifying color displayed on the optical sensor (S220).

Here, the optical sensor may be the optical sensor 10 of FIGS. 8 to 10. As described above, the optical sensor 10 includes a substrate, a reflective metal layer 110 disposed on the substrate, an insulator layer 120 disposed on the reflective metal layer 110 and a metal nanostructure layer 130 disposed on the insulator layer 120, the metal nanostructure layer 130 is a nanoisland network structure in which a plurality of metal nanoislands is connected, the insulator layer 120 includes a plurality of pillars p and a plurality of spaces v defined by the plurality of pillars p, and the plurality of spaces v may be filled with a fluid having the refractive index that is different from the refractive index of the plurality of pillars p.

After the optical sensor is prepared (S200), a sample is introduced into the optical sensor (S210).

Here, the sample may be a target for analysis. As the sample is introduced, the existing fluid in the plurality of spaces v of the optical sensor 10 may be replaced with the sample. As the plurality of spaces is filled with the second fluid, the effective dielectric constant value of the insulator layer may change, and the resonance wavelength may be shifted in the reflection spectrum. The color displayed on the optical sensor 10 may vary.

The color displayed on the optical sensor is identified (S220).

The refractive index of the sample may be analyzed by identifying the color displayed on the optical sensor 10. In the optical sensor 10 according to this embodiment, the resonance wavelength may be shifted by a predetermined interval in the reflection spectrum in response to the refractive index of each fluid. Because the resonance wavelength corresponds to a wavelength shift that can be detected in visible light, a color change displayed on the optical sensor 10 may be identified with naked eye. Accordingly, a database may be built using colors that the optical sensor 10 displays in response to the refractive index of the introduced fluid. That is, inverse analysis of the refractive index of the sample may be conducted by identifying color displayed on the optical sensor.

In an embodiment, in the fluid analysis method using an optical sensor, analysis of the refractive index of the sample may further include determining if the sample is toxic by identifying color that the toxic material displays in the optical sensor 10. That is, the fluid analysis method using an optical sensor may further include pre-organizing colors that representative toxic materials display in the optical sensor into a database, and determining if the sample is toxic.

The fluid analysis method using an optical sensor according to this embodiment may further include defining the sample to be analyzed based the refractive index of the sample.

The fluid analysis method using an optical sensor according to this embodiment may analyze the refractive index of the sample and define the toxicity and type in response to a change of visible light on site without using a specific light or a laser of high cost.

While the present disclosure has been hereinabove described with reference to the embodiments, the present disclosure should not be construed as being limited by these embodiments or drawings, and those skilled in the art will understand that various modifications and changes may be made to the present disclosure without departing from the spirit and scope of the present disclosure set forth in the appended claims.

What is claimed is:

1. A method for manufacturing an optical sensor, comprising:
    forming a reflective metal layer on a substrate;
    forming an insulator layer on the reflective metal layer;
    inducing self-assembly of a metal nanostructure layer including a plurality of nanoislands directly on the insulator layer opposite to the reflective metal layer without etching the metal nanostructure layer; and
    selectively etching the insulator layer using the self-assembled metal nanostructure layer as a mask to form a plurality of pillars under the plurality of nanoislands and a plurality of spaces defined by the plurality of pillars.

2. The method for manufacturing an optical sensor according to claim 1, wherein the plurality of pillars includes a hydrophobic material.

3. The method for manufacturing an optical sensor according to claim 2, wherein the hydrophobic material is amorphous fluoropolymer, and a refractive index of the plurality of pillars and a refractive index of the plurality of spaces are different.

4. The method for manufacturing an optical sensor according to claim 1, wherein the reflective metal layer is a gold thin film layer, and
    a metal applied to the self-assembly of the metal nanostructure layer is gold.

5. The method for manufacturing an optical sensor according to claim 1, wherein the forming of the reflective metal layer and the inducing of the self-assembly of the metal nanostructure layer are performed through a thermal evaporation process, and
    a thermal evaporation rate of the reflective metal layer is faster than a thermal evaporation rate of the nanostructure layer.

6. The method for manufacturing an optical sensor according to claim 5, wherein the thermal evaporation rate in inducing the self-assembly of the metal nanostructure layer is 0.3 Å/s.

7. The method for manufacturing an optical sensor according to claim 1, wherein the metal nanostructure layer is a nanoisland network structure in which the plurality of nanoislands is connected.

8. The method for manufacturing an optical sensor according to claim 1, wherein selectively etching the insulator layer is performed on portions of the insulator layer where the self-assembled metal nanostructure layer does not overlap.

* * * * *